United States Patent
Choe et al.

(10) Patent No.: US 9,113,814 B2
(45) Date of Patent: Aug. 25, 2015

(54) ENDOSCOPE APPARATUS CAPABLE OF PROVIDING NARROW BAND IMAGING AND IMAGE PROCESSING METHOD OF THE ENDOSCOPE APPARATUS

(75) Inventors: Won-hee Choe, Seoul (KR); Jae-guyn Lim, Seongnam-si (KR); Seong-deok Lee, Seongnam-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 547 days.

(21) Appl. No.: 13/243,542

(22) Filed: Sep. 23, 2011

(65) Prior Publication Data
US 2012/0220823 A1    Aug. 30, 2012

(30) Foreign Application Priority Data

Feb. 25, 2011   (KR) .................. 10-2011-0017292

(51) Int. Cl.
  A61B 1/06  (2006.01)
  A61B 1/00  (2006.01)
(52) U.S. Cl.
  CPC ........... A61B 1/0638 (2013.01); A61B 1/00009 (2013.01); A61B 1/0646 (2013.01); A61B 1/0684 (2013.01); A61B 1/0005 (2013.01)
(58) Field of Classification Search
  CPC .. A61B 1/0638; A61B 1/043; A61B 1/00186; A61B 1/00009; A61B 1/063; A61B 5/0059; H04N 2005/2255; H04N 2209/044; H04N 2207/045
  USPC .......................................... 600/160, 178, 181
  See application file for complete search history.

(56) References Cited

U.S. PATENT DOCUMENTS

| 7,704,206 | B2 | 4/2010 | Suzuki et al. |
| 2003/0229270 | A1* | 12/2003 | Suzuki et al. ................. 600/178 |
| 2005/0027166 | A1* | 2/2005 | Matsumoto et al. .......... 600/162 |
| 2008/0113317 | A1* | 5/2008 | Kemp et al. .................... 433/215 |
| 2009/0304243 | A1* | 12/2009 | Mertz et al. .................... 382/128 |
| 2010/0097454 | A1* | 4/2010 | Kubo et al. ....................... 348/65 |

FOREIGN PATENT DOCUMENTS

| JP | 05-232387 | 9/1993 |
| JP | 2001-087221 | 4/2001 |
| JP | 2002-95635 A | 4/2002 |
| JP | 2002-253500 | 9/2002 |
| JP | 2002-345733 | 12/2002 |
| JP | 2004-8412 A | 1/2004 |
| JP | 2007-089840 | 4/2007 |
| JP | 2007-268047 | 10/2007 |
| JP | 2008-085807 | 4/2008 |
| KR | 1020080007582 | 1/2008 |
| KR | 1020080020689 | 3/2008 |
| KR | 1020080030492 | 4/2008 |
| KR | 1020080051178 | 6/2008 |
| KR | 1020080102241 | 11/2008 |
| KR | 1020080102317 | 11/2008 |
| KR | 1020090030346 | 3/2009 |

* cited by examiner

Primary Examiner — Anhtuan T Nguyen
Assistant Examiner — Alexandra Newton
(74) Attorney, Agent, or Firm — NSIP Law

(57) ABSTRACT

An endoscope apparatus and image processing method of an endoscope apparatus are provided. In one respect, an endoscope apparatus includes an illumination unit for selectively providing light in a plurality of wavelength bands and white light, a sensing unit for receiving light reflected from a body cavity, and an image processing unit for generating additional synthesized images.

13 Claims, 7 Drawing Sheets

ENDOSCOPE APPARATUS CAPABLE OF PROVIDING NARROW BAND IMAGING AND IMAGE PROCESSING METHOD OF THE ENDOSCOPE APPARATUS

CROSS-REFERENCE TO RELATED APPLICATIONS

This application claims the benefit under 35 U.S.C. §119 (a) of Korean Patent Application No. 10-2011-0017292, filed on Feb. 25, 2011, in the Korean Intellectual Property Office, the disclosure of which is incorporated herein in its entirety by reference for all purposes.

BACKGROUND

1. Field

The following description relates to an endoscope apparatus and an image processing method of an endoscope apparatus, and more particularly, to an endoscope apparatus that provides narrow band imaging.

2. Description of the Related Art

An endoscope is a medical tool that may be inserted into a human body in order to provide observation of organs or a body cavity in which a lesion may not be directly observed without an operation or incision. An endoscope includes a narrow, long insertion portion for insertion into the human body to facilitate observation of organs in the body cavity. As image processing technology has developed, initially a black and white camera was used to capture an image of each part in the body cavity, and thus a lesion in each part may be examined in detail through a captured image. More recently, the simple black and white camera has been replaced by a high resolution color imaging device so that a lesion may be observed in more detail. Also, a chromo endoscope that captures an image after dying a surface of the body cavity with a particular pigment according to the type of a lesion to be identified has been used.

A narrow band imaging (NBI) endoscope has been suggested to improve lesion identification. The NBI endoscope is based on a principle that a depth of light penetrating tissue varies according to a wavelength of the light. For example, the NBI endoscope captures an image of each part in the body cavity using a blue, green, or red light of a narrow wavelength band, instead of only using a general white light of a wide wavelength band. Accordingly, an image of a surface, a middle part, or a deep part of a mucous membrane in the body cavity may be obtained according to a wavelength of the light in use. Thus, a lesion may be more easily identified according to differences among the obtained images. The NBI endoscope may be used to determine, for example, esophageal angiodysplasia or a stomach cancer in an early stage that does not protrude yet, tumor lesion of a large intestine, and loss of normal vessels.

As one example, the NBI endoscope separates a visible light of a wide band into blue, green, or red light of narrow bands using a rotary filter wheel. The separated narrow band light is sequentially or selectively illuminated onto a particular part of a body cavity to obtain an image.

SUMMARY

Provided is a narrow band imaging (NBI) endoscope apparatus providing improved lesion identification, while including a relatively simple structure and image processing.

Also provided is a method for processing an image in the NBI endoscope apparatus.

According to one aspect, an endoscope apparatus includes an illumination unit which selectively provides a white light and a plurality of additional lights, each of the plurality of additional lights having a different wavelength band, a sensing unit which receives light reflected from a body cavity, the sensing unit generating a color image captured by the white light and a plurality of images of different wavelength bands captured by the plurality of additional lights having different wavelength bands, and an image processing unit which generates additional synthesized images by combining the plurality of images of different wavelength bands generated by the sensing unit.

The illumination unit may include a white light source and a filter member including a plurality of different band pass filters.

The white light source may emit light of an infrared (IR) wavelength band and light of a visible wavelength band.

The filter member may include a first band pass filter including a first pass band and a second pass band that does not overlap the first pass band, a second band pass filter including a third pass band that partially overlaps the first pass band and also partially overlaps the second pass band, and a third band pass filter including a fourth pass band that partially overlaps the second pass band.

The filter member may include a first band pass filter including a first pass band and a second pass band that does not overlap the first pass band, and a fourth band pass filter including a third pass band and a fourth pass band, wherein the third pass band partially overlaps the first and second pass band, and wherein the fourth pass band that partially overlaps the second pass band.

A first overlapping band comprising an overlapping band of the first pass band and the third pass band may correspond to a wavelength band of blue light, a second overlapping band comprising an overlapping band of the second pass band and the third pass band may correspond to a wavelength band of green light, and a third overlapping band comprising an overlapping band of the second pass band and the fourth pass band may correspond to a wavelength band of IR light.

The sensing unit may be configured to generate a first image according to light captured with respect to the first and second pass bands, a second image according to light captured with respect to the third pass band, and a third image according to light captured with respect to the fourth pass band.

The image processing unit may be configured to convert the first to third images generated by the sensing unit into a plurality of converted binary images, and the image processing unit is also configured to generate a plurality of generated binary images for each color by performing an AND operation on binary images having substantially the same color of a plurality of converted binary images.

The image processing unit may be configured to generate additional images by combining at least two of the plurality of generated binary images.

The illumination unit may include a red light source which emits light in a wavelength band of red light, a green light source which emits light in a wavelength band of green light, a blue light source which emits light in a wavelength band of blue light, and an IR light source which emits light in a wavelength band of IR light.

The endoscope apparatus may be configured to operate in at least one of an RGB mode and a narrow band mode, the illumination unit may be configured to turn on the red light source, the green light source, and the blue light source in the RGB mode and to turn off the IR light source in the RGB mode, and the illumination unit may be configured to turn off the red light source, the green light source, and the blue light source in the narrow band mode and to turn on the IR light source in the narrow band mode.

The sensing unit may be configured to generate a red band image corresponding to a wavelength band of red light, a green band image corresponding to a wavelength band of green light, and a blue band image corresponding to a wavelength band of blue light in the RGB mode, and the sensing unit may be configured to generate an IR band image corresponding to a wavelength band of IR light in the narrow band mode.

The image processing unit may be configured to synthesize a plurality of additional images by combining at least two selected from the group of the red band image, the green band image, the blue band image, the IR band image, and any combination thereof.

The endoscope apparatus may further include a display device configured to display at least one selected from the group of the color image generated by the sensing unit, the plurality of images of different wavelength bands captured by the plurality of additional light, the synthesized images generated by the image processing unit, and any combination thereof.

According to another aspect, there is provided a method of processing an image in an endoscope apparatus includes illuminating at least a portion of a body cavity by a plurality of lights, each of the plurality of lights having a plurality of different wavelength bands, receiving light reflected from the at least a portion of the body cavity, the received light corresponding to at least two different wavelength bands of the plurality of lights, generating at least two images according to the received light, converting the at least two images to a plurality of converted binary images, generating a plurality of generated binary images by performing an AND operation on binary images having substantially the same wavelength band of the plurality of converted binary images, generating additional images by combining at least two of the plurality of generated binary images, and displaying the generated additional images on a display device.

The at least two images may include at least two of: a first image generated by light of a first wavelength band and a second wavelength band, wherein the first and second wavelength bands do not overlap, a second image generated by light of a third wavelength band, wherein the third wavelength band partially overlaps the first and second wavelength bands, and a third image generated by light of a fourth wavelength band, wherein the fourth wavelength band that partially overlaps the second wavelength band.

The at least two images may include a first image generated by light of a first wavelength band and a second wavelength band, wherein the first and second wavelength bands do not overlap, and a second image captured by light of a third wavelength band and a fourth wavelength band, wherein the third wavelength band partially overlaps the first and second wavelength bands, and wherein the fourth wavelength band partially overlaps the second wavelength band.

A first overlapping band may include an overlapping band of the first wavelength band and the third wavelength band and may correspond to a wavelength band of blue light, a second overlapping band may include an overlapping band of the second wavelength band and the third wavelength band may correspond to a wavelength band of green light, and a third overlapping band may include an overlapping band of the second wavelength band and the fourth wavelength band may correspond to a wavelength band of IR light.

The generating of a plurality of binary images for each color may include generating a binary image corresponding to a wavelength band of blue light by converting an image component of a first image captured by a blue sub-pixel to a first binary image, converting an image component of a second image captured by the blue sub-pixel to a second binary image, and performing an AND operation on the first binary image and the second binary image, generating a binary image corresponding to a wavelength band of IR light by converting an image component of the first image captured by a green sub-pixel to a third binary image, converting an image component of the second image captured by the green sub-pixel to a fourth binary image, and performing an AND operation on the third binary image and the fourth binary image, and generating a binary image corresponding to a wavelength band of IR light by converting an image component of the first image captured by a red sub-pixel to a fifth binary image, converting an image component of the third image captured by the red sub-pixel to a sixth binary image, and performing an AND operation on the fifth binary image and the sixth binary image.

Prior to the illuminating of the at least a portion of the body cavity, the method may include checking for a suspicious lesion portion in the at least a portion of the body cavity by illuminating the at least a portion of the body cavity with a white light that includes light of an IR wavelength band and light of a visible band.

The method may further include determining, with respect to the at least two images, whether the at least a portion of the body cavity includes a suspicious lesion portion, and illuminating another portion of the body cavity if the at least a portion of the body cavity does not include a suspicious lesion portion.

The method may further include determining, with respect to the generated additional images, whether the at least a portion of the body cavity includes a suspicious lesion portion, and illuminating another portion of the body cavity if the at least a portion of the body cavity does not include a suspicious lesion portion.

According to another aspect of the present invention, a method of processing an image in an endoscope apparatus includes illuminating at least a portion of a body cavity by a visible light emitted from a red light source, a green light source, and a blue light source, while an IR light source does not emit light, receiving visible light reflected from the at least a portion of the body cavity, generating a red band image, a green band image, and a blue band image according to light respectively received in red, green, and blue wavelength bands, illuminating the at least a portion of the body cavity by an IR light emitted from the IR light source while the red light source, the green light source, and the blue light source do not emit light, receiving IR light reflected from the at least a portion of the body cavity, generating an IR band image according to light received in an IR wavelength band, synthesizing a plurality of additional images by combining at least two selected from the group of the red band image, the green band image, the blue band image, the IR band image, and any combination thereof, and displaying, on a display device, at least one selected from the group of the red band image, the green band image, the blue band image, the plurality of additional images, and any combination thereof.

The synthesizing of a plurality of additional different images may include combining of the blue band image and the green band image, the blue band image and the red band image, the blue band image and the IR band image, the green band image and the red band image, the green band image and the IR band image, and the red band image and the IR band image.

Other features and aspects may be apparent from the following detailed description, the drawings, and the claims.

Figure 1:
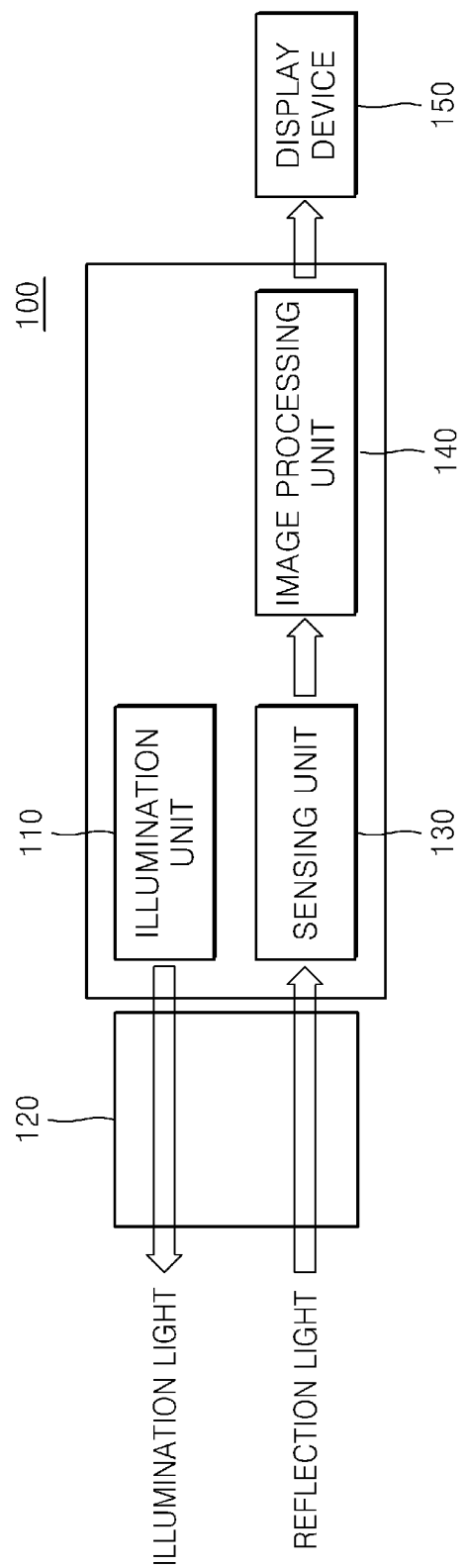
FIG. 1 is a block diagram schematically illustrating an example of an endoscope apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 illustrates an example of an endoscope apparatus 100. Referring to FIG. 1, the endoscope apparatus 100 includes an illumination unit 110, a sensing unit 130, and an image processing unit 140. The illumination unit 110 selectively provides light in one or more of a plurality of relatively narrow wavelength bands, as well as white light of a relatively wide wavelength band. The sensing unit 130 is configured to receive light in a relatively wide band, including an infrared wavelength band and a visible band, and generates an image. The image processing unit 140 may generate additional narrow band images synthesized according to images of different wavelength bands generated by the sensing unit 130. The endoscope apparatus 100 may further include a light transmission member 120 that transmits light generated by the illumination unit 140 to a desired location in a body cavity. However, when the illumination unit 110 and the sensing unit 130 are directly inserted in the body cavity, the light transmission member 120 may not be employed. Also, the endoscope apparatus 100 may further include a display device 150 that displays an image generated by the image processing unit 140.

Figure 2:
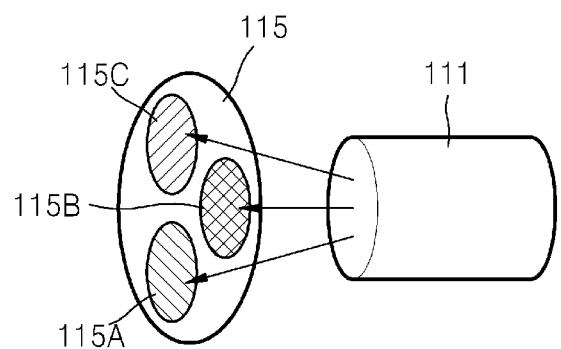
FIG. 2 is a diagram schematically illustrating an example of the illumination unit of FIG. 1.

FIG. 2 illustrates an example of the illumination unit 110 of FIG. 1. Referring to FIG. 2, the illumination unit 110 may include a light source 111 and a filter member 115 that includes a plurality of various band pass filters. The light source 111 may be implemented as a white light source that emits a white light of a relatively wide band, including an infrared (IR) band. For example, a xenon lamp may be used as the light source 111. The filter member 115, arranged in front of the light source 111, may transmit only light of a particular wavelength band from the white light emitted from the light source 111. The filter member 115 may be removed from an optical path by a mechanical transfer device, such that the white light emitted from the light source 111 travels along the optical path without passing through the filter member 115. For example, when a white light is to be provided to a particular portion of the body cavity, the filter member 115 may be removed from the optical path. Also, when light of a particular wavelength band is to be provided, the filter member 115 may be positioned in the optical path, that is, arranged in front of the light source 111.

Also, the filter member 115 may include a plurality of band pass filters 115A, 115B, and 115C having different pass bands. Although three band pass filters (115A, 115B, and 115C) are illustrated in FIG. 2, they are merely provided as an example, and the number of the band pass filters may be changed according to design or selection choice. In one implementation, the filter member 115 may be manufactured in form of a general rotary filter wheel. As one example, a plurality of band pass filters, each having a fan shape, is combined to form a single thin disc type filter member. As another example, a plurality of band pass filters, each having a circular or polygonal shape is sequentially arranged in an azimuth direction on a thin disc type substrate. The filter member 115 may be rotated or moved such that any one of the band pass filters 115A, 115B, and 115C is located on the optical path. Then, of the white light emitted by the light source 111, only a light having a particular wavelength band, after passing through one of the band pass filters 115A, 115B, and 115C located on the optical path, may be provided to the inside of the body cavity.

Figure 3:
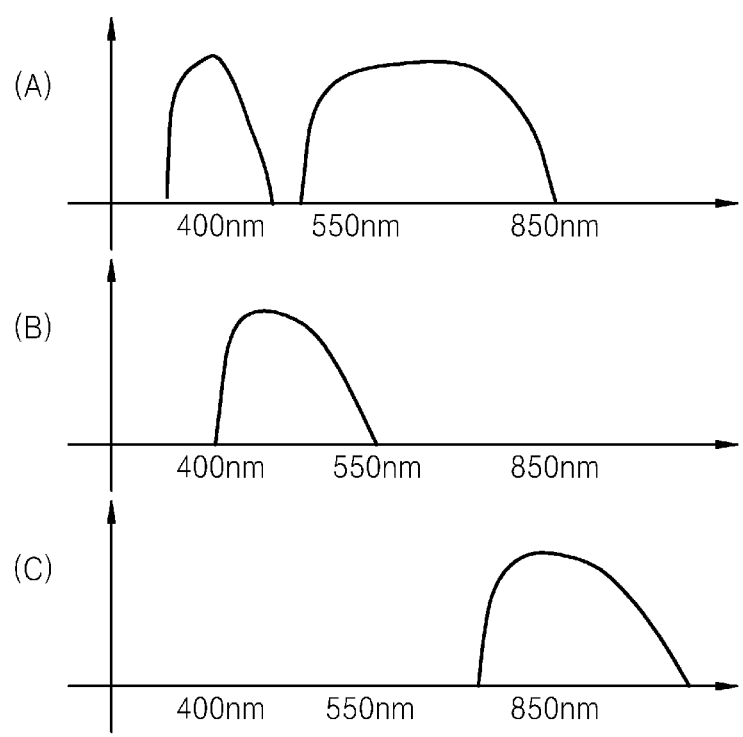
FIG. 3 illustrates examples of graphs of pass bands of the filters included in the illumination unit of FIG. 2.

FIG. 3 illustrates graphs of pass bands of the filters included in the illumination unit of FIG. 2. Referring to FIG. 3, the first band pass filter 115A may have a double pass band including a first pass band of about 380-450 nm and a second pass band of about 540-780 nm. The second band pass filter 115B may have a third pass band of about 400-560 nm. The third band pass filter 115C may have a fourth pass band of about 720-860 nm. Thus, the third pass band of the second band pass filter 115B may partially overlap the first and second pass bands of the first band pass filter 115A. Also, the fourth pass band of the third band pass filter 115C may partially overlap the second pass band of the first band pass filter 115A.

Figure 4:
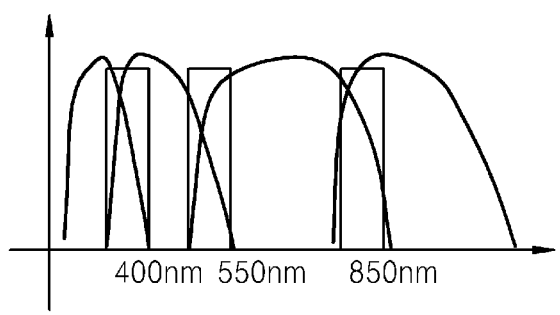
FIG. 4 is a graph illustrating an example of overlapping bands of the pass bands of the filters of FIG. 3.

FIG. 4 is a graph illustrating an example of the overlapping bands of the pass bands illustrated in FIG. 3. Referring to FIG. 4, a first overlapping band between the first pass band of the first band pass filter 115A and the third pass band of the second band pass filter 115B may be about 400-450 nm, corresponding to a blue wavelength band. A second overlapping band between the second pass band of the first band pass filter 115A and the third pass band of the second band pass filter 115B may be about 540-560 nm, corresponding to a green wavelength band. A third overlapping band between the second pass band of the first band pass filter 115A and the fourth pass band of the third band pass filter 115B may be about 720-780 nm, corresponding to an infrared wavelength band. However, it should be understood that in other examples of the filter member 115, values corresponding to the first to fourth pass bands and the first to third overlapping bands of the first to third band pass filters 115A, 115B, and 115C may vary.

Figure 5:
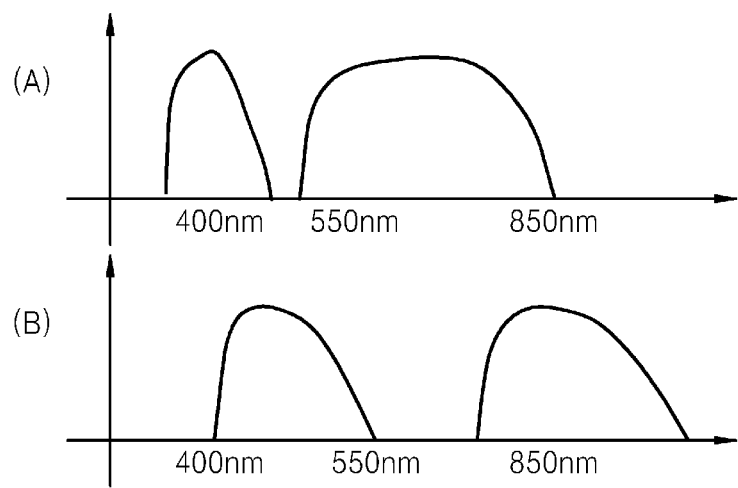
FIG. 5 illustrates other examples of graphs of pass bands of filters.

Although in the above example only the first band pass filter 115A has a double pass band, the second band pass filter 115B may also have a double pass band. For example, as illustrated in FIG. 5, the first band pass filter 115A may have a double pass band including a first pass band of about 380-450 nm and a second pass band of about 540-780 nm. The second band pass filter 115B may have a double pass band including a third pass band of about 400-560 nm and a fourth pass band of about 720-860 nm. In this example, the third band pass filter 115C may not be used. That is, the filter member 115 may include only the first band pass filter 115A and the second band pass filter 115B. Accordingly, the first and second band pass filters 115A and 115B may have three overlapping bands that are similar to those illustrated in FIG. 4.

The light transmission member 120 is generally formed as a narrow, long insertion unit that may be inserted into a body cavity. The light transmission member 120 may provide the light emitted by the illumination unit 110 into the body cavity to illuminate a particular portion of the body cavity. Also, the light transmission member 120 may transmit light reflected from an illuminated portion of the body cavity to the sensing unit 130. To transmit light, the light transmission member 120 may include, for example, a plurality of optical fiber bundles (not shown). Since the light transmission member 120 may be similar to that used in a general endoscope apparatus, a detailed description of the light transmission member 120 is omitted herein.

Figure 6:
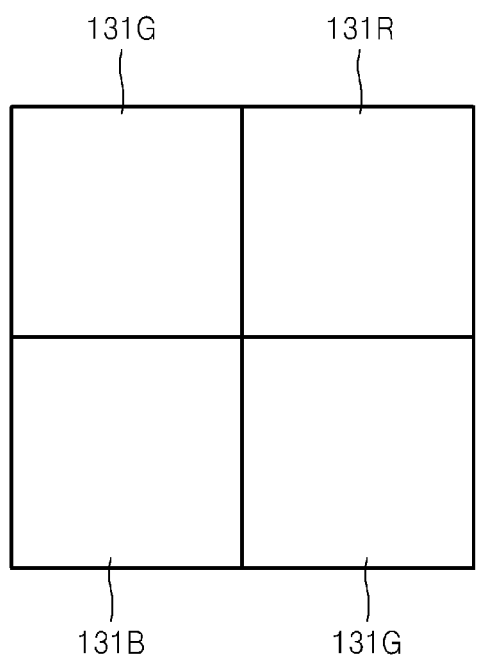
FIG. 6 is a diagram illustrating an example of a single photodetection pixel of the sensing unit of FIG. 1.

The sensing unit 130 senses the reflection light transmitted by the light transmission member 120 and forms an image of the illuminated portion of the body cavity according to the reflection light. To sense light, the sensing unit 130 may include a plurality of photodetection pixels arranged in a 2D array. FIG. 6 illustrates an example of a single photodetection pixel 131 of the sensing unit 130 of FIG. 1. Referring to FIG. 6, the single photodetection pixel 131 of the sensing unit 130 may include four sub-pixels. For example, each pixel 131 of the sensing unit 130 may include two green sub-pixels 131G arranged in a first diagonal direction and a red sub-pixel 131R and a blue sub-pixel 131B that are arranged in a second diagonal direction. That is, the sub-pixels may be arranged as in a general Bayer sensor method. Also, for example, a CMOS image sensor or a CCD image sensor may be used as a photodetection device of the sub-pixels 131R, 131G, and 131B. Further, other implementations of photodetection pixel 131 may be applicable, according to design or selection choice.

In the examples described herein, the sensing unit 130 may be configured to sense not only visible light, but also light in an infrared (IR) band. In a typical sensing module, an IR cut-off filter is arranged on a front surface of the CMOS image sensor or CCD image sensor. Accordingly, the sensing unit 130 may use a typical sensing module in which an IR cut-off filter is removed.

Figure 7:
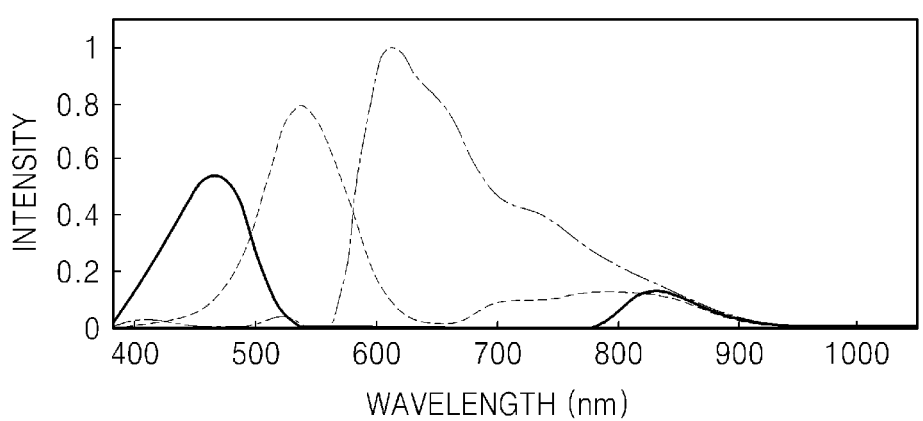
FIG. 7 is a graph illustrating an example of sensitivity according to a wavelength of the photodetection pixel of the sensing unit of FIG. 6.

FIG. 7 is a graph illustrating an example of sensitivity according to a wavelength of the above-described sensing unit 130. Referring to FIG. 7, the sensing unit 130 may be configured to have sensitivity over a wide range, for example, from a blue wavelength band to an infrared wavelength band.

The image processing unit 140 may provide an additional image that is synthesized using images obtained from light of different wavelength bands. Accordingly, the image processing unit 140 may provide a narrow band image (NBI) having a high lesion contrast. For example, the image processing unit 140 may extract only NBIs corresponding to the first to third overlapping bands illustrated in FIG. 4 from the images obtained from the sensing unit 130, using each of the first to third band pass filters 115A, 115B, and 115C. By appropriately combining the NBIs of the first to third overlapping bands, the image processing unit 140 may generate an image with an increased lesion contrast. A method of generating an image of the image processing unit 140 will be further described herein.

Figure 8:
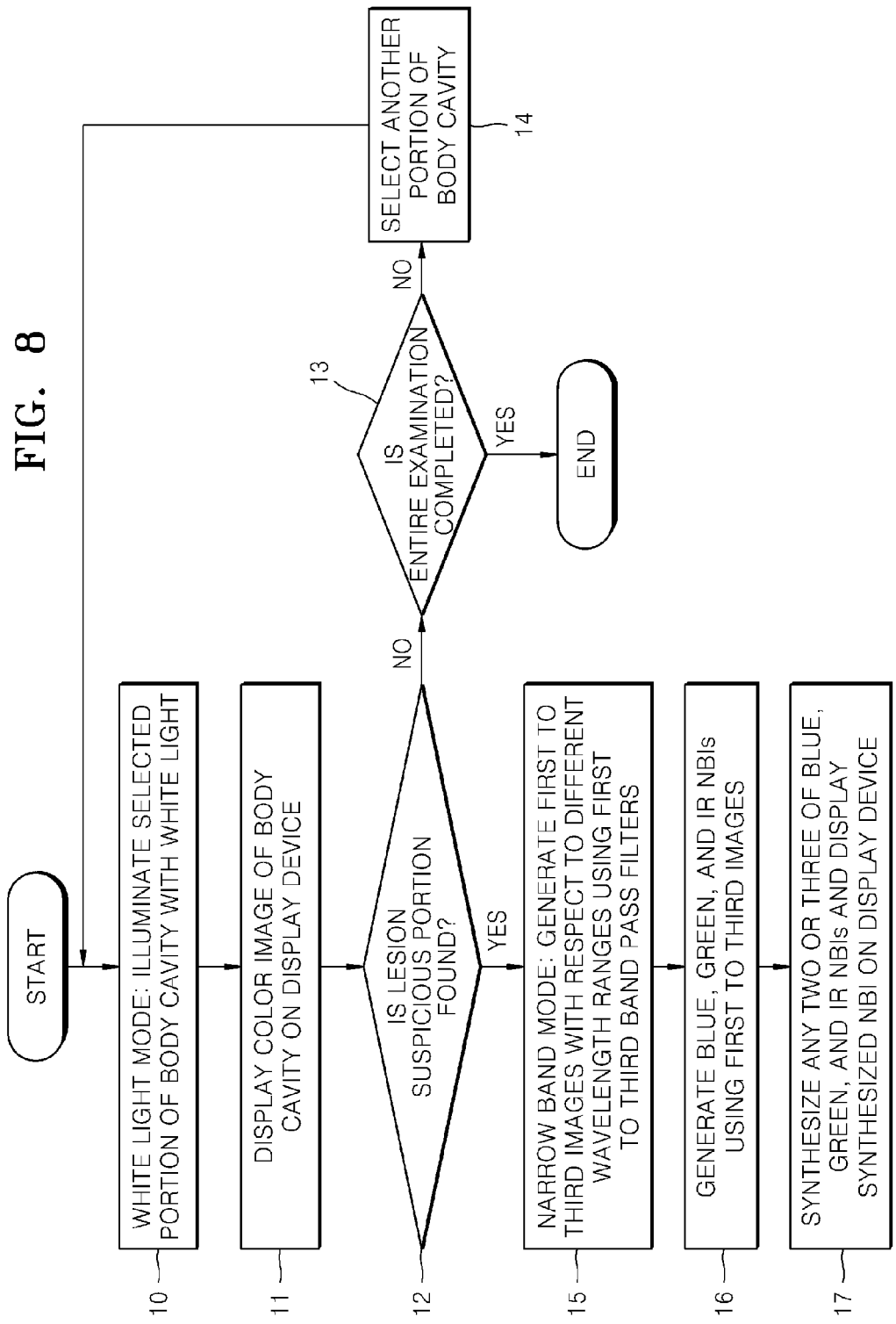
FIG. 8 is a flowchart illustrating an example of an operation of the endoscope apparatus of FIG. 1.

The operation of the endoscope apparatus 100 configured as above is described herein with reference to FIG. 8. Referring to FIG. 8, in operation S10 the endoscope apparatus 100 is in a white light mode for illuminating a body cavity with a white light. For example, an end portion of the light transmission member 120 is inserted into the body cavity to be examined and a white light is provided to a selected portion of the body cavity through the light transmission member 120. Accordingly, for this operation, the filter member 115 may be removed from the front surface of the light source 111 that emits the white light. That is, the white light emitted by the light source 111 may be transmitted into the body cavity through the light transmission member 120 without being filtered. Light reflected from the selected portion of the body cavity that is illuminated by the white light is transmitted back to the sensing unit 130 via the light transmission member 120. The sensing unit 130 may generate a color image of the selected portion of the body cavity according to the reflected light. Thus, in an operation S11, the color image of the body cavity generated by the sensing unit 130 may be displayed on the display device 150 in substantially real time.

In operation S12, a user may observe a color image displayed on the display device 150 to check for any suspicious lesion portion. If a suspicious lesion portion is not found, observation may continue by selecting another portion of the body cavity in operation S14. When an examination on all portions of the body cavity is completed in the above manner, the entire examination may be completed (operation S13).

However, if a suspicious lesion portion is found in a particular portion of the body cavity, the endoscope apparatus 110 may enter a narrow band mode for generating NBI to more accurately identify a lesion in operation S15. Accordingly, the filter member 115 is arranged in front of the light source 111. As one example, light is transmitted in an order of the first band pass filter 115A, the second band pass filter 115B, and the third band pass filter 115C, thereby generating an image for each wavelength band (with respect to the pass bands illustrated in FIG. 3). That is, by arranging the first band pass filter 115A in an optical path, a selected portion of the body cavity is illuminated by the light of the first pass band and the second pass band. The sensing unit 130 may generate a first image captured by optical components of the first and second pass bands. Further, the filter member 115 may be rotated by a predetermined angle so that the second band pass filter 115B is arranged in the optical path. Accordingly, the selected portion of the body cavity is illuminated by the light of the third pass band. Thus, the sensing unit 130 may generate a second image captured by an optical component of the third pass band. Finally, the filter member 115 may be rotated again by a predetermined angle so that the third band pass filter 115C is arranged in the optical path. As a result, the sensing unit 130 may generate a third image captured by an optical component of the fourth pass band.

As another example, if the filter member 115 only includes two band pass filters having the pass bands illustrated in FIG. 5, two different images may be obtained. For example, a first image captured by the optical components of the first and second pass bands and a fourth image captured by the optical components of the third and fourth pass bands may be obtained. For convenience of explanation, a method of using first to third images captured using the first to third band pass filters 115A, 115B, and 115C will be described. Since the fourth image may be regarded to be an image obtained by synthesizing the second image and the third image, the following description may be also applied to an example using two band pass filters having the pass bands illustrated in FIG. 5.

In operation S16, the image processing unit 140 generates NBIs of blue, green, and infrared bands, using the first to third images generated by the sensing unit 130. For example, blue narrow band imaging (B-NBI) may be generated as follows. The image processing unit 140 converts an image component captured by the blue sub-pixel 131B of the sensing unit 130 from the first image obtained by the first band pass filter 115A to a first binary image having values 0 and 1 according to luminosity. The image processing unit 140 converts an image component captured by the blue sub-pixel 131B of the sensing unit 130 from the second image obtained by the second band pass filter 115B to a second binary image having values 0 and 1 according to luminosity. An AND operation may be performed on the first and second binary images to obtain the B-NBI.

Also, green narrow band imaging (G-NBI) may be generated as follows. The image processing unit 140 converts an image component captured by the green sub-pixel 131G of the sensing unit 130 from the first image obtained by the first band pass filter 115A to a third binary image having values 0 and 1 according to luminosity. The image processing unit 140 converts an image component captured by the green sub-pixel 131G of the sensing unit 130 from the second image obtained by the second band pass filter 115B to a fourth binary image having values 0 and 1 according to luminosity. An AND operation may be performed on the third and fourth binary images to obtain the G-NBI.

Finally, infrared narrow band imaging (IR-NBI) may be generated as follows. The image processing unit 140 converts an image component captured by the red sub-pixel 131R of the sensing unit 130 from the first image obtained by the first band pass filter 115A to a fifth binary image having values 0 and 1 according to luminosity. The image processing unit 140 converts an image component captured by the red sub-pixel 131R of the sensing unit 130 from the third image obtained by the third band pass filter 115C to a sixth binary image having values 0 and 1 according to luminosity. An AND operation may be performed on the fifth and sixth binary images to obtain the IR-NBI.

The B-NBI obtained as described above may be, for example, an image of a band of about 415±30 nm. The G-NBI obtained as described above may be, for example, an image of a band of about 540±30 nm. The IR-NBI obtained as described above may be, for example, an image of a band of about 740±20 nm.

Any one of or all of the three binary NBIs (B-NBI, G-NBI, and IR-NBI) generated as described above may be sequentially or simultaneously displayed on the display device 150 according to a user's selection. Also, in operation S17, the image processing unit 140 may generate an image obtained by synthesizing two of the three binary NBIs according to the users selection. For example, the image processing unit 140 may generate an image obtained by synthesizing the B-NBI and the G-NBI, an image obtained by synthesizing the B-NBI and the IR-NBI, or an image obtained by synthesizing the G-NBI and the IR-NBI. As a further example, an image may be generated by synthesizing all of the B-NBI, G-NBI, and IR-NBI according to the users selection. Each of the synthesized images may be displayed on the display device 150. Further, each of the synthesized images may be a new NBI image.

According to the examples described herein, a plurality of binary images is obtained by binarizing an image generated by each sub-pixel of the sensing unit 130. Since the plurality of binary images is synthesized without using a separate image processing method, a method for obtaining NBI may be performed in a relatively simple manner. Also, according to the examples described herein, since at least one band pass filter having a double pass band is used, light loss is relatively low, thereby providing relatively brighter and clearer NBIs. Furthermore, since a near IR having a relatively deep penetration depth is used, a lesion contrast may be increased with respect to a deeper area in the body cavity, as compared to a conventional NBI endoscope.

In the above description, a process of generating NBI using the white light source 111 and the filter member 115 is provided. However, in another example, NBI may be obtained using a plurality of light sources that emit light of different wavelength bands.

Figure 9:
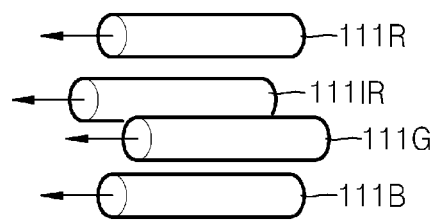
FIG. 9 is a diagram schematically illustrating another example of the illumination unit of FIG. 1.
Figure 10:
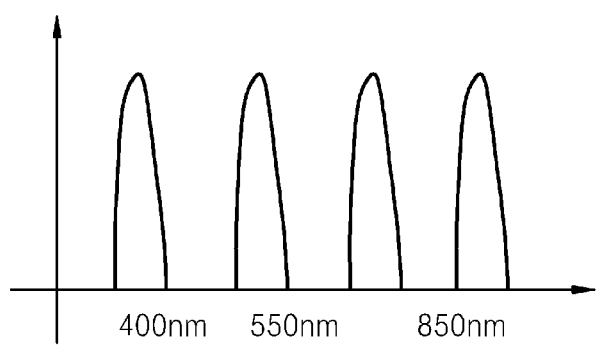
FIG. 10 is a graph illustrating examples of light emitting wavelength bands of light sources of the illumination unit of FIG. 9.

FIG. 9 schematically illustrates an example where the illumination unit 110 includes a plurality of light sources, each emitting a different wavelength band. Referring to FIG. 9, the illumination unit 110 may include a red light source 111R, a green light source 111G, a blue light source 111B, and an IR light source 111IR. FIG. 10 illustrates a graph of an example of light emitting wavelength bands of the light sources 111R, 111G, 111B, and 111IR. As one example, the blue light source 111B may be a blue light emitting diode (LED) that emits light of a range of about 380-450 nm. The green light source 111G may be a green LED that emits light of a range of about 500-560 nm. The red light source 111R may be a red LED that emits light of a range of about 600-660 nm. The IR light source 111IR may be an IR LED that emits light of a range of about 720-800 nm. In the present example, the structure of the other parts of the endoscope apparatus 100 other than the illumination unit 110 may be similar to the above-described structure with regard to FIG. 1. However, an image processing method of the image processing unit 140 may be different from that described with respect to FIG. 8.

Figure 11:
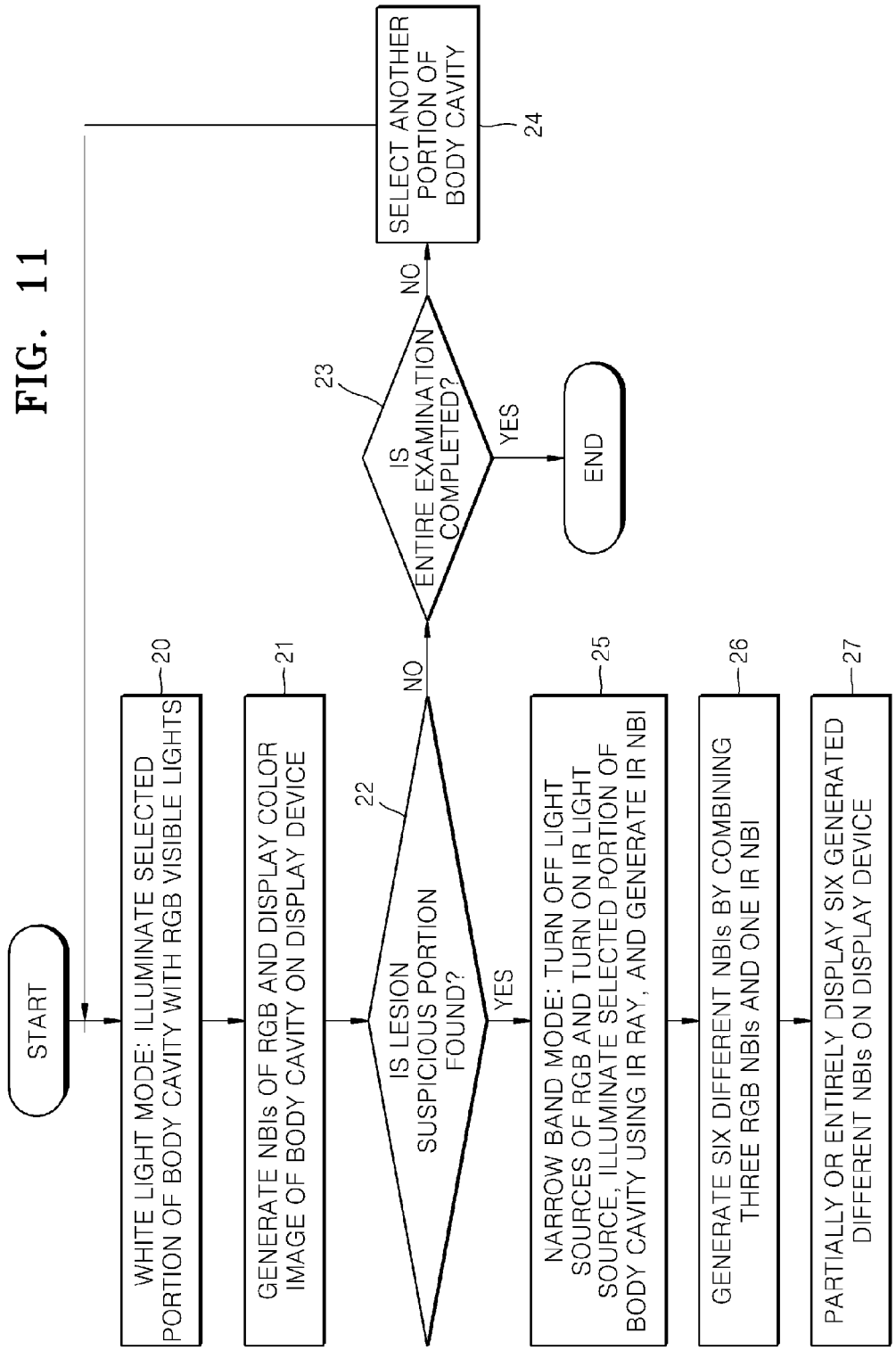
FIG. 11 is a flowchart illustrating another example of an operation of an endoscope apparatus.

The operation of the endoscope apparatus 100 having a plurality of light sources that are different from one another is described herein with reference to FIG. 11.

Referring to FIG. 11, in operation S20 the endoscope apparatus 100 is in an RGB mode in which a body cavity is illuminated with a visible light only including RGB. For example, of the red light source 111R, the green light source 111G, the blue light source 111B, and the IR light source 111IR, only the IR light source 111IR is turned off in the RGB mode, whereas the other red, green, and blue light sources 111R, 111G, and 111B are each turned on. Accordingly, RGB light emitted by the red, green, and blue light sources 111R, 111G, and 111B illuminates a selected portion of the body cavity via the light transmission member 120 that is inserted into the body cavity. Light reflected from the selected portion of the body cavity that is illuminated is transmitted to the sensing unit 130 via the light transmission member 120. Thus, in operation S21, the sensing unit 130 may generate a color image with respect to the selected portion of the body cavity according to the reflected light. That is, the sensing unit 130 may generate each of red NBI (R-NBI) obtained from the red sub-pixel 131R, green NBI (G-NBI) obtained from the green sub-pixel 131G, and blue NBI (B-NBI) obtained from the blue sub-pixel 131B. The sensing unit 130 may also generate a single color image obtained by synthesizing the red, green, and blue NBIs. The color image generated by the sensing unit 130 may be displayed on the display device 150 in substantially real time.

In operation S22, a user may identify a suspicious lesion portion by observing the color image displayed on the display device 150. If a suspicious lesion portion is not found, another portion of the body cavity may be selected to continue the examination in operation S24. When an examination on all portions of the body cavity is completed in the above manner, the entire examination may be terminated in operation S23.

However, if a lesion suspicious portion is found in a particular portion of the body cavity, the endoscope apparatus 110 may enter a narrow band mode for generating NBI to more accurately identify a lesion in operation S25. For example, of the red light source 111R, the green light source 111G, the blue light source 111B, and the IR light source 111IR, only the IR light source 111IR is turned on in the narrow band mode, whereas the other red, green, and blue light sources 111R, 111G, and 111B are each turned off. Accordingly, IR light emitted by the IR light source 111IR illuminates a selected portion of the body cavity via the light transmission member 120 that is inserted into the body cavity. IR light reflected from the selected portion of the body cavity that is illuminated is transmitted to the sensing unit 130 via the light transmission member 120. Thus, the sensing unit 130 may generate an IR NBI of the selected portion of the body cavity. In the above process, three NBIs, that is, red, green, and blue NBIs, may be obtained in the RGB mode and a single NBI, that is, an IR NBI, may be obtained in the narrow band mode. The B-NBI may be, for example, an image of a band of about 415±30 nm. The G-NBI may be, for example, an image of a band of about 540±30 nm. The R-NBI may be, for example, an image of a band of about 650±20 nm. The IR-NBI may be, for example, an image of a band of about 740±20 nm.

In operation S26, the image processing unit 140 may generate six synthesized different images having increased lesion contrast by combining the three NBIs obtained in the RGB mode (that is, the red, green, and blue NBIs) and the one NBI obtained in the narrow band mode (that is, the IR NBI). For example, the image processing unit 140 may generate a new image by combining the blue NBI and the green NBI, the blue NBI and the red NBI, the blue NBI and the IR NBI, the green NBI and the red NBI, the green NBI and the IR NBI, and the red NBI and the IR NBI, according to a user's selection. Thus, by synthesizing image information of two different colors, a new image having an increased lesion contrast may be obtained. In operation S27, the above synthesized new NBIs may be partially or entirely displayed on the display device 150 according to a users selection. Furthermore, as another example, any or all of the NBIs obtained in the RGB mode and synthesized NBIs may be sequentially or simultaneously displayed on the display device 150 according to a user's selection.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An endoscope apparatus comprising:
   an illumination unit configured to selectively provide a white light and additional lights having respective different wavelength bands;
   a sensing unit configured to
     receive light reflected from a body cavity, and
     generate a color image captured by the white light, and images of the respective different wavelength bands that are captured by the additional lights, the sensing unit comprising a red sub-pixel, a green sub-pixel, and a blue sub-pixel; and
   an image processing unit configured to
     generate a blue narrow band image by converting image components captured by the blue sub-pixel from the respective images to blue binary images, respectively, and performing an AND operation on the blue binary images,
     generate a green narrow band image by converting image components captured by the green sub-pixel from the respective images to green binary images, respectively, and performing an AND operation on the green binary images,
     generate an IR narrow band image by converting image components captured by the red sub-pixel from the respective images to red binary images, respectively, and performing an AND operation on the red binary images, and
     generate a synthesized image by combining at least two of the blue, green, and IR narrow band images.

2. The endoscope apparatus of claim 1, wherein the illumination unit comprises a white light source and a filter member comprising different band pass filters.

3. The endoscope apparatus of claim 2, wherein the white light source is configured to:
   emit light of an infrared (IR) wavelength band and light of a visible wavelength band.

4. The endoscope apparatus of claim 2, wherein the filter member comprises:
   a first band pass filter comprising a first pass band and a second pass band that does not overlap the first pass band;
   a second band pass filter comprising a third pass band that partially overlaps the first pass band and also partially overlaps the second pass band; and
   a third band pass filter comprising a fourth pass band that partially overlaps the second pass band.

5. The endoscope apparatus of claim 2, wherein the filter member comprises:
   a first band pass filter comprising a first pass band and a second pass band that does not overlap the first pass band; and
   a fourth band pass filter comprising a third pass band and a fourth pass band, wherein the third pass band partially overlaps the first pass band and also partially overlaps the second pass band, and wherein the fourth pass band partially overlaps the second pass band.

6. The endoscope apparatus of claim 4, wherein:
   a first overlapping band of the first pass band and the third pass band corresponds to a wavelength band of blue light;
   a second overlapping band of the second pass band and the third pass band corresponds to a wavelength band of green light; and
   a third overlapping band of the second pass band and the fourth pass band corresponds to a wavelength band of IR light.

7. The endoscope apparatus of claim 5, wherein:
a first overlapping band of the first pass band and the third pass band corresponds to a wavelength band of blue light;
a second overlapping band of the second pass band and the third pass band corresponds to a wavelength band of green light; and
a third overlapping band of the second pass band and the fourth pass band corresponds to a wavelength band of IR light.

8. The endoscope apparatus of claim 4, wherein the sensing unit is configured to:
generate a first image captured by light of the first and second pass bands, a second image captured by light of the third pass band, and a third image captured by light of the fourth pass band.

9. The endoscope apparatus of claim 1, wherein the illumination unit comprises:
a red light source configured to emit light in a wavelength band of red light;
a green light source configured to emit light in a wavelength band of green light;
a blue light source configured to emit light in a wavelength band of blue light; and
an IR light source configured to emit light in a wavelength band of IR light.

10. The endoscope apparatus of claim 9, wherein:
the endoscope apparatus is configured to operate in an RGB mode and a narrow band mode; and
the illumination unit is configured to
turn on the red light source, the green light source, and the blue light source, and turn off the IR light source, in the RGB mode, and
turn off the red light source, the green light source, and the blue light source, and turn on the IR light source, in the narrow band mode.

11. The endoscope apparatus of claim 10, wherein the sensing unit is configured to:
generate a red band image corresponding to the wavelength band of red light, a green band image corresponding to the wavelength band of green light, and a blue band image corresponding to the wavelength band of blue light, in the RGB mode; and
generate an IR band image corresponding to the wavelength band of IR light, in the narrow band mode.

12. The endoscope apparatus of claim 11, wherein the image processing unit is configured to:
generate additional images by combining at least two of the red band image, the green band image, the blue band image, and the IR band image.

13. The endoscope apparatus of claim 1, further comprising:
a display device configured to display at least one of the color image, the images of the respective different wavelength bands, and the synthesized image.

* * * * *